United States Patent [19]

Chau et al.

[11] 4,320,087
[45] Mar. 16, 1982

[54] LABORATORY ASSAY DEVICE

[75] Inventors: Kue H. Chau, Mundelein, Ill.; Robert A. Beard, Kenosha, Wis.

[73] Assignee: Abbott Laboratories, North Chicago, Ill.

[21] Appl. No.: 871,268

[22] Filed: Jan. 23, 1978

[51] Int. Cl.³ .................. G01N 33/54; G01N 33/56
[52] U.S. Cl. .......................... 422/69; 23/915; 23/920; 422/71; 422/101; 422/102
[58] Field of Search .............. 23/253 R, 230 B, 915, 23/920; 128/272; 422/61, 68, 69, 71, 99, 101, 102

[56] References Cited

U.S. PATENT DOCUMENTS

| | | | |
|---|---|---|---|
| 2,812,231 | 11/1957 | Zar | 128/272 X |
| 2,856,930 | 10/1958 | Huyck et al. | 128/272 |
| 3,437,206 | 4/1969 | Kusik | 23/253 R X |
| 3,539,300 | 11/1970 | Stone | 23/230 B X |
| 3,545,930 | 12/1970 | Walker et al. | 23/253 R X |
| 3,635,678 | 1/1972 | Seitz et al. | 23/230 B X |
| 3,646,346 | 2/1972 | Catt | 23/230 B X |
| 3,932,141 | 1/1976 | Beall et al. | 23/230 B X |

*Primary Examiner*—Arnold Turk
*Attorney, Agent, or Firm*—John J. McDonnell

[57] ABSTRACT

A device useful in the performance of a variety of immunologic and biochemical assays which comprises a container enclosing a solid phase reagent with an adsorbent and a retaining means for prohibiting the removal of said solid phase reagent is disclosed. The device is particularly well adapted to perform heterogeneous immunoassays and to permit processing large numbers of said immunoassays by facilitating the separation of assay medium from the solid phase reagents.

2 Claims, 5 Drawing Figures

LABORATORY ASSAY DEVICE

BACKGROUND OF THE INVENTION

When performing radioimmunoassays, enzyme-immunoassays and competitive protein binding assays, it is often necessary to separate the antigen-antibody complex or protein ligand complex from other components in the assay. Methods previously used to achieve this separation include the addition of a liquid phase reagent to cause a precipitate in the assay medium and the introduction of a heterogeneous phase material into the assay medium which is easily separated at the end of the assay.

Examples of the liquid phase method include (a) the fractional precipitation of proteins using salts or solvents which allow the proteins to retain their binding capabilities even in their precipitate forms and (b) the precipitation of the antibody with a second antibody against it.

Examples of the separation of reaction components employing the addition of heterogeneous phase materials include (a) the adsorption of free nitrogen with surface active sorbents such as charcoal, talc, microfine silica and resin; (b) the formation of antigen-antibody complexes on supports on which first or second antibody has been permanently linked; (c) the formation of antigen-antibody complexes on pre-precipitated second antibody particles; and (d) the formation of antigen-antibody complexes on the inside surface of tubes on which antibody has been immobilized.

With the exception of the coated tubes and coated solid supports, all liquid phase and heterogeneous phase reagents require centrifugation to separate precipitate or solid material from the assay medium. This step is not only time consuming, but often requires special or delicate handling of the material when removing supernatant fluid. If the assay result is time dependent, only a small number of tests can be processed to assure accurate timing. Although the coated tube avoids these separation problems and is simple to use, it suffers from very low binding capacity and poor consistency from lot to lot because of manufacturing difficulties.

Solid supports, sorbent or protein coated, that do not require centrifugation to separate them from the liquid medium have been most recently developed to perform in heterogeneous assays. However, they must be dispensed initially by the technician performing the assay. Normally this is not a serious limitation, but in the situation where the solid support has been coated with pathogenic antigens or radio-labeled reagents, it is best if the dispensing of the solid support can be obviated. Also, aspiration of the supernatant liquid is required to separate the solid support and absorbed components from the reaction medium at the end of the assay.

SUMMARY OF THE INVENTION

The claimed invention discloses a device which is useful in the performance of immunologic and biochemical assays which comprises: a container having an opening for the introduction and removal of reagents; a solid phase reagent situated within said container; and a retaining means positioned proximal to the opening in said container to prohibit the removal of said solid phase reagent from within said container.

The solid phase reagent is large enough so as not to require centrifugation to settle in the assay medium and to be retained within the reaction container by retaining means when the container is inverted to decant the reaction medium. The retaining means obviates the limitations of conventional heterogeneous reagents and permits a large number of assays to be processed at high speed by facilitating precise dispensation and decantation of reagents.

DESCRIPTION OF THE PREFERRED EMBODIMENTS

Figure 1:
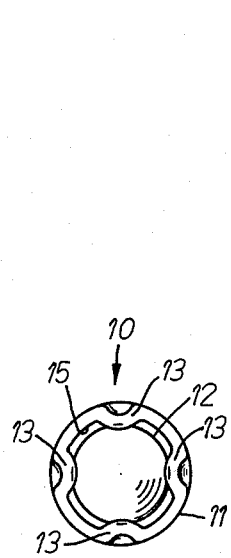
FIG. 1 is a perspective view showing the front and top of the disclosed device.
Figure 3:
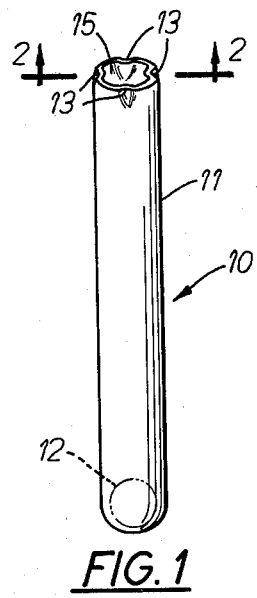
FIG. 3 is a top view of the disclosed device showing the solid phase reagent being confined within the container by one embodiment of the retaining means.
Figure 4:
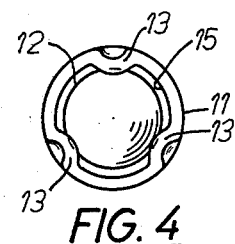
FIG. 4 is a top view of the disclosed device showing the solid phase reagent being confined within the container by a second embodiment of the retaining means.
Figure 2:
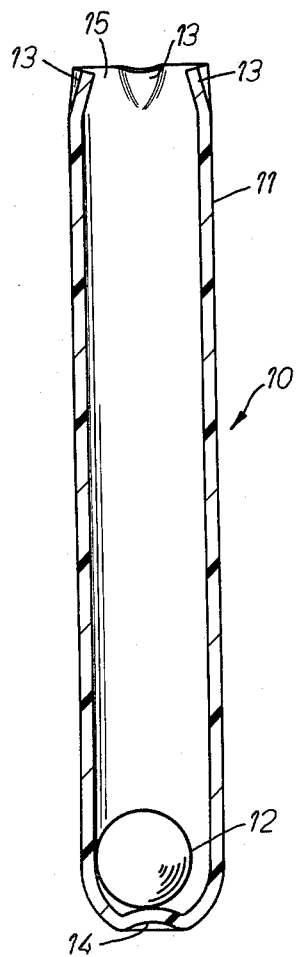
FIG. 2 is a partial cross-section taken along line 2—2.
Figure 5:
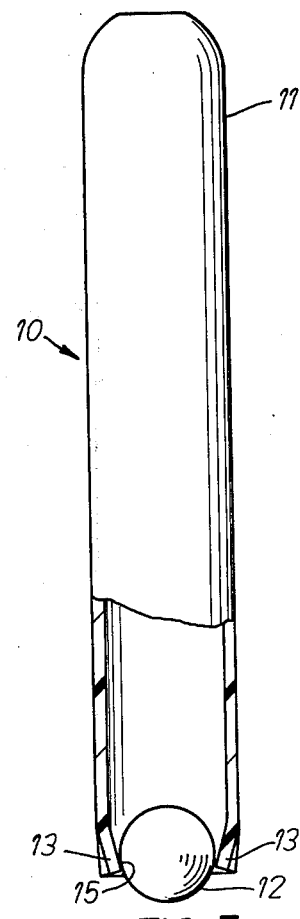
FIG. 5 is a partial cross-section of the disclosed device illustrating the retention of the solid phase reagent with the container when said container is inverted to decant the assay medium.

An elaboration of the claimed device will be undertaken with reference to the accompanying drawings.

The device 10 is essentially a container 11 having an opening 15 for the introduction and removal of reagents. The container 11 is ideally fashioned from a plastic, polymeric material but could just as well be fabricated from metal or glass. The shape of the container 11 is of no particular importance; however, most assays can be conducted conveniently in elongated containers resembling test tubes.

The solid phase reagent 12 is situated within the container 11. It should be of a size convenient to move freely within the container 11, but large enough to interact or provide a sufficient quantity of component for the performance of the assay. The solid phase reagent 12 may be conveniently fashioned from any plastic, polymeric material. Other solid materials such as glass, metal or chemically treated paper could also be employed, but the suitability of a plastic material is difficult to ignore.

The solid phase reagent 12 may be coated, impregnated or fashioned entirely of adsorbents, immunoadsorbents, immunoreactants or labeled components thereof. It may be a carrier or vehicle of immunoreactants to be released into the reaction medium in quantities proportional to the quantity of unknown to be assayed. Conceivably, these immunoreactants may be labeled with radioactive isotopes, enzymes or fluorescent moieties to assist in the determination of quantities of reactant employed in the assay.

Solid phase reagents 12 considered within the scope of this invention will include solid plastic beads coated with a variety of materials to aid in the performance in an equally diverse number of assays. Examples of coating that have proven useful include activated charcoal, talc, resin and the like. These sorbents enable the solid phase reagent to separate components in biochemical assays by adsorbing particular molecules. Other adsorbent coatings include immunoadsorbents such as antigens, antibodies and complexes thereof. Similarly, these coatings facilitate the separation and removal of any immunoreactant having an affinity for the particular coating employed.

The solid support 12 should be of a size to fit easily within the confines of said container 11, and present adequate surface area for the optimum performance of the assay. A spherical, styrene bead has been found to possess a surface which can be coated easily with any of the aforementioned adsorbents and provide the desired surface area.

When employing the preferred embodiment of the claimed device, it is advisable to provide a dimple 14 in the bottom of the tubular container 11 so that the spherical bead 12 does not seat and become immobilized within the bottom curvature of the container. This inconvenience may also be remedied by providing a bead with a spherical radius less than that of the tubular container.

The function of the retaining means 13 is simply to retain the solid phase reagent 12 within the container 11 and thereby facilitate the separation of the adhered reaction components from those remaining in the assay medium at the conclusion of the assay reaction. The retaining means 13 should be positioned proximal to the container opening 15 so as to permit maximum mobility of the solid phase reagent 12 within the container. Ideally, the retaining means 13 should be fashioned so as to allow the removal of the assay medium while retaining the solid support. In other words, it would serve no purpose for the retaining means to be situated so that the retained solid phase reagent 12 would block the opening 15 of the container and prevent the removal of the assay medium.

The retaining means 13 could assume a variety of forms and configurations. For instance, a simple cap for the container 11 with a hole or a number of holes might be suitably employed. A springlike device wedged within the container 11 near the opening would also function within the scope of the claimed invention.

The drawings illustrate two variations of one very practical approach: crimping. Reducing the diameter of the container 11 by crimping at the or near the opening 15 is a convenient and inexpensive method for providing a retaining means 13. The crimping may consist of one or a series of indentations with the only requirements being that a single crimp be large enough to retain the solid reagent and that an inordinately large number of crimps not impede the removal if assay medium while retaining the solid reagent.

If retention of the solid phase regent is to be achieved by crimping the sides of a plastic container, the protrusions may be formed in a number of ways. The container could have protrusions molded in or formed by the application of localized heat. An approach found to be particularly useful is to use a polypropylene container 12×75 mm and ultrasonically deform the plastic at the rim of the container to form a suitable retaining means for the solid phase reagent.

The preferred embodiment of the claimed device would retain the solid support 12 but permit its extension beyond the lip of the opening. This would permit the technician to remove excess reaction medium from the surface of the solid phase reagent by rotating the confined reagent, like a ball in a socket, on an adsorbent paper or towel.

As mentioned above, this disclosed device is particularly useful for performing radio or enzyme immunoassays for biochemical entities such as hormones, drugs, antigens, antibodies and the like. A typical assay would be performed by (1) pipetting specimens or standards into the container 11 already containing a confined solid phase reagent; (2) adding a reagent containing radio or enzyme labeled components similar to those in the specimen to be assayed; (3) incubating the mixture for a specific period; (4) decanting the liquid from the container by inverting and retaining the solid phase reagent within said container; and (5) measuring the radio or enzyme activity in the tubes.

The foregoing elaboration has been offered to promote an appreciation and understanding of the disclosed device and no unnecessary limitations should be assumed therefrom. Specifically,

What is claimed is:

1. A device useful for conducting immunologic and biochemical assays which comprises:
    (a) a reaction vial having an opening for the introduction and removal of reagents;
    (b) an adsorbent solid phase freely movable within said vial; and
    (c) means integral with said vial and positioned proximal to said opening to retain and prohibit removal of said adsorbent solid phase but permitting removal of nonadsorbed reagents wherein the adsorbent solid phase is a support coated with activated charcoal.

2. A device useful for conducting immunologic and biochemical assays which comprises:
    (a) a reaction vial having an opening for the introduction and removal of reagents;
    (b) an adsorbent solid phase freely movable within said vial; and
    (c) means integral with said vial and positioned proximal to said opening to retain and prohibit removal of said adsorbent solid phase but permitting removal of nonadsorbed reagents wherein the adsorbent solid phase is a polystyrene bead with a coating of activated charcoal.

* * * * *